US009554958B2

(12) United States Patent
Richards et al.

(10) Patent No.: US 9,554,958 B2
(45) Date of Patent: Jan. 31, 2017

(54) SYSTEM AND METHOD FOR DETECTION OF INFANT PRESENCE

(71) Applicant: General Electric Company, Schenectady, NY (US)

(72) Inventors: Andrew H. Richards, Westminster, MD (US); James Patrick Cipriano, Laurel, MD (US)

(73) Assignee: General Electric Company, Schenectady, NY (US)

( * ) Notice: Subject to any disclaimer, the term of this patent is extended or adjusted under 35 U.S.C. 154(b) by 11 days.

(21) Appl. No.: 14/102,562

(22) Filed: Dec. 11, 2013

(65) Prior Publication Data

US 2015/0161868 A1 Jun. 11, 2015

(51) Int. Cl.
| | |
|---|---|
| *F24F 11/00* | (2006.01) |
| *A61B 5/11* | (2006.01) |
| *A61G 11/00* | (2006.01) |
| *A61B 5/00* | (2006.01) |
| *G08B 21/22* | (2006.01) |

(52) U.S. Cl.
CPC .............. *A61G 11/00* (2013.01); *A61B 5/1115* (2013.01); *A61B 5/6892* (2013.01); *A61B 2503/04* (2013.01); *A61B 2560/0209* (2013.01); *A61B 2562/0247* (2013.01); *A61B 2562/0252* (2013.01); *F24F 11/0034* (2013.01); *G08B 21/22* (2013.01)

(58) Field of Classification Search
CPC . F24F 11/0034; F24F 11/0009; A47C 21/048; A61F 2007/0096; A61G 2203/36; A61G 7/001; A61G 7/05769; A61N 5/0613; E05B 81/77; E05B 81/78; F05B 2220/60; F05B 2220/602; F24D 19/10; F24D 2220/208

USPC ...... 340/573.1, 666, 309.7, 438, 457, 539.1, 340/606, 665, 667, 668; 600/22, 301, 534
See application file for complete search history.

(56) References Cited

U.S. PATENT DOCUMENTS

| | | | | |
|---|---|---|---|---|
| 5,088,645 | A | * | 2/1992 | Bell ................... G05D 23/1902 165/11.1 |
| 5,162,038 | A | * | 11/1992 | Wilker ............................ 600/22 |
| 5,162,838 | A | | 11/1992 | Inuzuka et al. |
| 5,684,460 | A | * | 11/1997 | Scanlon ..................... 340/573.1 |
| 5,902,255 | A | * | 5/1999 | Ogino ........................... 600/595 |
| 5,948,303 | A | * | 9/1999 | Larson ............... G05D 23/1905 126/205 |

(Continued)

OTHER PUBLICATIONS

International Search Report and Written Opinion from corresponding PCT application No. PCT/US2014/055639 mailed on Dec. 12, 2014; 9 pages.

*Primary Examiner* — Fekadeselassie Girma

(57) ABSTRACT

A system and method for controlling the operation of an infant care device based upon whether the infant care device is occupied or unoccupied. One or more sensors are positioned within the infant care device to determine whether the infant care device is occupied or unoccupied. A controller receives the indication of the occupied status of the infant care device and operates the infant care device in a selected mode of operation. Upon a change in the occupied status of the infant care device, the controller adjusts various operating parameters and alarm parameters. The controller continuously monitors the occupied status of the infant care device and controls the operation of the infant care device accordingly.

14 Claims, 3 Drawing Sheets

(56) References Cited

U.S. PATENT DOCUMENTS

| | | | | |
|---|---|---|---|---|
| 6,154,621 | A * | 11/2000 | Yamamoto | G03G 15/657 347/153 |
| 6,377,177 | B1 * | 4/2002 | Broussard et al. | 340/573.1 |
| 6,396,403 | B1 * | 5/2002 | Haner | 340/573.4 |
| 6,443,885 | B1 | 9/2002 | Schuler | |
| 6,515,586 | B1 * | 2/2003 | Wymore | 340/541 |
| 6,819,249 | B1 * | 11/2004 | Papp | 340/573.1 |
| 6,892,405 | B1 * | 5/2005 | Dimitriu | A61G 7/001 5/609 |
| 7,035,432 | B2 * | 4/2006 | Szuba | 382/103 |
| 7,106,207 | B1 * | 9/2006 | Marchan | 340/667 |
| 7,170,401 | B1 * | 1/2007 | Cole | 340/457 |
| 7,218,218 | B1 * | 5/2007 | Rogers | 340/522 |
| 7,319,382 | B1 * | 1/2008 | Vu | 340/457 |
| 7,567,181 | B1 * | 7/2009 | Davison | 340/573.1 |
| 7,701,358 | B1 * | 4/2010 | White et al. | 340/667 |
| 7,823,972 | B2 * | 11/2010 | Browne et al. | 297/217.2 |
| 8,364,647 | B1 * | 1/2013 | Eastlund et al. | 707/666 |
| 8,599,025 | B2 * | 12/2013 | Cipriano | 340/573.1 |
| 8,672,842 | B2 * | 3/2014 | Kenalty et al. | 600/300 |
| 8,795,151 | B2 * | 8/2014 | Falk et al. | 600/22 |
| 2002/0084903 | A1 * | 7/2002 | Chaco | 340/573.1 |
| 2004/0164856 | A1 * | 8/2004 | Mesina | 340/457.1 |
| 2004/0201487 | A1 * | 10/2004 | Benson et al. | 340/666 |
| 2004/0236174 | A1 * | 11/2004 | Boone et al. | 600/21 |
| 2005/0215844 | A1 * | 9/2005 | Ten Eyck et al. | 600/22 |
| 2005/0215845 | A1 * | 9/2005 | Mahony et al. | 600/22 |
| 2006/0017579 | A1 * | 1/2006 | Albert et al. | 340/628 |
| 2006/0085102 | A1 * | 4/2006 | Doel et al. | 701/14 |
| 2006/0103516 | A1 * | 5/2006 | Zang | 340/457 |
| 2007/0052529 | A1 * | 3/2007 | Perez | 340/457 |
| 2007/0075575 | A1 * | 4/2007 | Gregory et al. | 297/217.3 |
| 2007/0132578 | A1 * | 6/2007 | Powell | 340/539.26 |
| 2007/0135675 | A1 * | 6/2007 | MacKin et al. | 600/22 |
| 2007/0276202 | A1 * | 11/2007 | Raisanen et al. | 600/301 |
| 2008/0015457 | A1 * | 1/2008 | Silva | 600/534 |
| 2008/0024311 | A1 * | 1/2008 | Mann | 340/573.1 |
| 2009/0189771 | A1 * | 7/2009 | Liu | 340/573.1 |
| 2009/0219279 | A1 * | 9/2009 | Ishii | G02B 26/0833 345/214 |
| 2010/0018249 | A1 * | 1/2010 | Burgers | F17C 5/06 62/657 |
| 2010/0187219 | A1 * | 7/2010 | Besore | G06Q 50/06 219/494 |
| 2010/0253141 | A1 * | 10/2010 | Cara | E05B 81/78 307/9.1 |
| 2010/0277328 | A1 * | 11/2010 | Mullan et al. | 340/665 |
| 2011/0006887 | A1 * | 1/2011 | Shaull | G05B 15/02 340/12.37 |
| 2011/0071698 | A1 * | 3/2011 | Glasser | F03B 13/00 700/296 |
| 2011/0241867 | A1 * | 10/2011 | Neal | 340/457 |
| 2012/0103963 | A1 * | 5/2012 | Milfeldt et al. | 219/218 |
| 2012/0128025 | A1 * | 5/2012 | Huppi | G01K 1/16 374/121 |
| 2012/0130200 | A1 * | 5/2012 | Cipriano | 600/301 |
| 2012/0174868 | A1 * | 7/2012 | Pinand | 119/60 |
| 2012/0261481 | A1 * | 10/2012 | Donlan | H05B 1/0275 237/12 |
| 2012/0295483 | A1 * | 11/2012 | Smed | 439/620.21 |
| 2013/0088344 | A1 * | 4/2013 | Rose et al. | 340/438 |
| 2013/0109342 | A1 * | 5/2013 | Welch | 455/404.2 |
| 2013/0109931 | A1 * | 5/2013 | Ng et al. | 600/301 |
| 2013/0158339 | A1 | 6/2013 | Cipriano et al. | |
| 2013/0274836 | A1 * | 10/2013 | Downs | A61N 5/0613 607/88 |
| 2013/0282198 | A1 * | 10/2013 | Kneuer et al. | 700/300 |
| 2013/0300198 | A1 * | 11/2013 | Yamashina et al. | 307/39 |
| 2014/0015664 | A1 * | 1/2014 | Watson | 340/457.1 |
| 2014/0253314 | A1 * | 9/2014 | Rambadt et al. | 340/457.1 |
| 2014/0294728 | A1 * | 10/2014 | McClung, III | 424/9.2 |
| 2014/0361889 | A1 * | 12/2014 | Wall et al. | 340/539.11 |
| 2015/0005588 | A1 * | 1/2015 | Herken | A61B 7/04 600/301 |
| 2015/0038072 | A1 * | 2/2015 | Cordier et al. | 455/39 |
| 2015/0039942 | A1 * | 2/2015 | Che | G06F 11/3612 714/38.1 |
| 2015/0091740 | A1 * | 4/2015 | Bai et al. | 340/901 |
| 2015/0100167 | A1 * | 4/2015 | Sloo | G01N 27/02 700/278 |

* cited by examiner

SYSTEM AND METHOD FOR DETECTION OF INFANT PRESENCE

BACKGROUND OF THE INVENTION

The present disclosure relates to an infant care device and a method for operating the infant care device that adjusts the operation based upon the presence of an infant. More specifically the present disclosure relates to a system and method that adjusts alarm parameters and operating modes of the infant care device based upon whether the infant care device is occupied or unoccupied.

Premature infants are often placed within an infant care device so that they may have a controlled and monitored environment to aid in their survival and growth. Premature infants are fragile and, as such, require a highly controlled environment. As such, currently available infant care devices include a highly automated control system to maintain the temperature within the infant care device environment and to monitor the physiological state of the infant. Typically, once the infant care device has been turned on the infant care device operates in a normal operating mode to control the temperature environment within the infant care device. If the infant is removed, the caregiver must manually indicate that the infant has been removed. This manual indication by the caregiver requires the caregiver to carry out additional steps, which are often difficult depending upon whether the caregiver has a free hand or time to enter such manual indication. Thus, it has been recognized that it would be desirable to have a system and method that automatically determines whether the infant care device is occupied or unoccupied without requiring the caregiver to manually enter such status.

SUMMARY OF THE INVENTION

The present disclosure generally relates to a system and method for controlling the operation of an infant care device. The system and method of the present disclosure determines whether an infant is present within the infant care device and modifies the operation of the infant care device based upon the occupied status.

The system of the present disclosure includes an infant platform that is positioned to support an infant within the device. One or more sensors are utilized to generate signals that indicate whether the infant platform is either occupied or unoccupied. The one or more sensors can be selected from a group that includes at least a camera, a motion detector, a temperature sensor, a pressure sensor, an $SpO_2$ Sensor and a microphone.

Based upon the determination of whether an infant is present on the infant platform, a controller of the infant care device controls the operation of the device. Specifically, the controller controls the Operation of the device in a first mode when the device is occupied and controls the operation of the infant care device in a second mode when the device is unoccupied. The adjustments to the operation of the infant care device can include modifying alarm parameters, controlling the heating of the interior of the infant care device and generating alerts based upon the transitions between an occupied state and an unoccupied state.

In accordance with the present disclosure, the controller operates the infant care device by initially receiving a signal from at least one sensor associated with the infant care device. The signal from the sensor indicates an infant presence state of the infant care device. Upon receiving this information, the controller operates the infant care device based upon the presence state. The operation of the infant care device depends upon whether the device is either occupied or unoccupied. The changes in the operation of the infant care device can include adjusting the alarm parameters and adjusting the heating control depending upon the presence state detected.

The method continues to monitor the signals from the sensors to determine the presence state of the infant care device. If the presence state changes, the controller modifies the operation of the infant care device.

When the infant care device is initially started, the method determines the presence state of the infant care device. If the controller determines that the infant care device does not include an infant, the controller enters into a preheat mode. However, if an infant is detected, the controller begins a normal mode of operation.

When the controller determines that an infant is present, the controller continues to operate in the normal mode. If the controller determines that the presence state changes, thereby indicating the removal of the infant, the controller can generate an alert to one of multiple selected locations within a hospital environment. The alert generated by the controller enhances the security of the hospital to prevent improper movement of infants.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
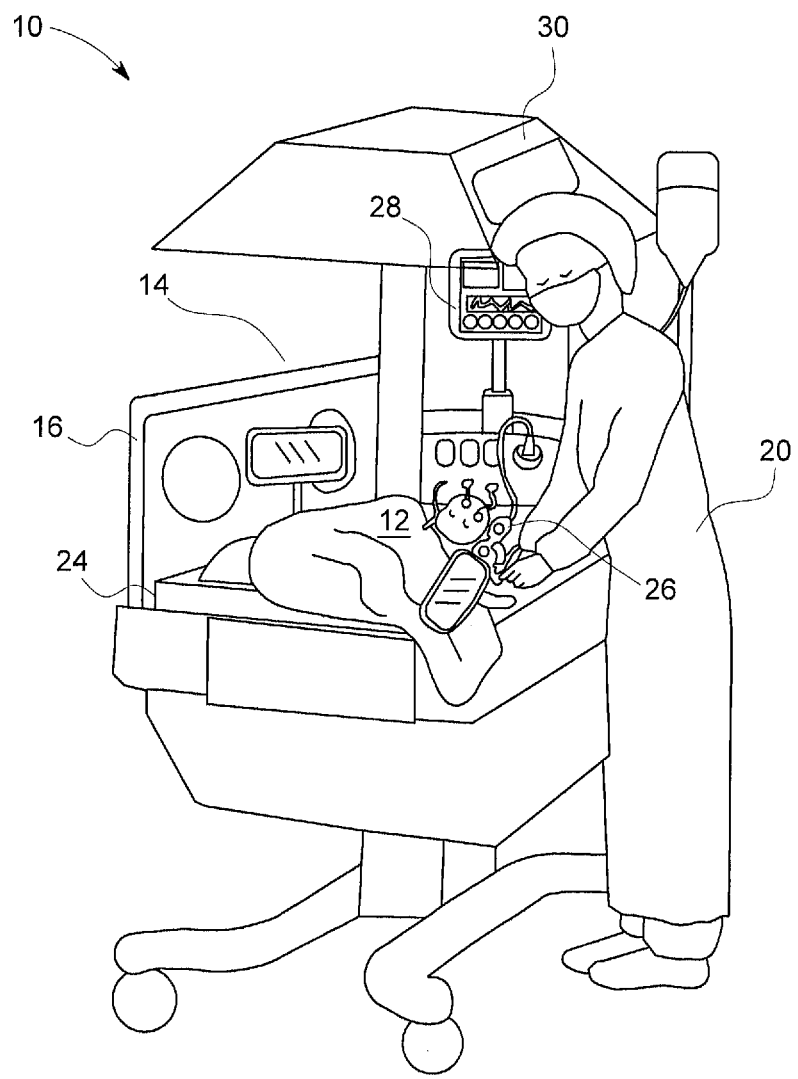
FIG. 1 is a detailed view of the infant care device in accordance with the present disclosure.

FIG. 1 illustrates one embodiment of an infant care device 10 that incorporates the method of detecting the presence of an infant 12 in accordance with the present disclosure. The infant care device 10 shown in FIG. 1 could be many different types of devices, such as an incubator-type infant care device or a patient warmer. The incubator-type infant care device shown in FIG. 1 defines a micro environment region 14 in which the infant rests and receives therapy, including heating and possible oxygen enrichment.

As illustrated in FIG. 1, the sides 16 of the infant care device 10 can be lowered such that a caregiver 20 can have access to the infant 12 positioned on an infant platform 24, such as a mattress. Various different patient sensors 26 can be attached to the infant such that the infant care device 10 can monitor physiological parameters from the infant. The various different types of sensors that can be utilized in accordance with the present disclosure will be fully described in greater detail below.

The monitored physiological parameters are shown on a display 28 and can be viewed by the caregiver 20. As illustrated in FIG. 1, a relatively significant number of devices may be positioned on the infant platform 24 along with the infant 12. These components can include intravenous tubes, pillows, blankets, patient sensors and other similar components. In the embodiment shown in FIG. 1, a radiant heating hood 30 is positioned above the infant 12 and heats the micro environment region 14, and thus the infant 12, as desired. As described previously, it is desirable that the infant 12 remains within the micro environment region 14 created by the infant care device 10 such that the patient remains warm.

Figure 2:
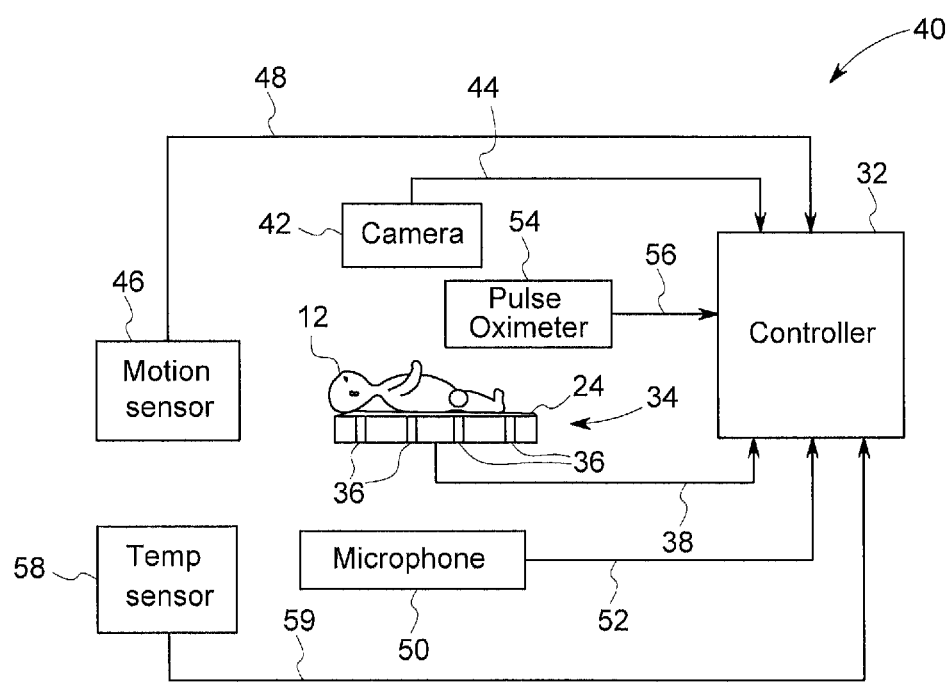
FIG. 2 is a schematic representation of the monitoring sensors utilized with the infant care device of the present disclosure.

Although not shown in FIG. 1, the infant care device 10 includes a scale that determines the weight of the infant 12 and displays the weight on the display 28. The scale 34 is positioned beneath the infant platform 24 and is shown in FIG. 2 as communicating with a controller 32 for the infant care device. The scale 34 includes a series of pressure sensors 36 that generate signals along control line 38 that allow the controller 32 to determine the weight of the infant 12.

FIG. 2 illustrates an infant presence sensing system 40 constructed in accordance with the present disclosure. The infant presence sensing system 40 includes a series of separate sensors that each communicates signals to the controller 32. Based upon the signals from the various sensors shown in FIG. 2, the controller 32 can determine an infant presence state for the infant care device. Specifically, the controller 32 can determine whether the infant care device is occupied or unoccupied by an infant 12. Based upon this determination, the controller 32 can selectively control the operation of the infant care device to optimize the operation of the infant care device based upon the determined presence or non-presence of the infant.

As described above, the infant presence sensing system 40 may include various different sensors that each communicate to the controller 32. In the representative embodiment shown in FIG. 2, the system includes a camera 42 positioned to view the entire interior of the infant care device 10 and provide a signal to the controller 32 along the communication line 44. Either the camera 42 or the controller 32 can have the required operating components to detect a change in the image from the camera 42 indicating either the presence or absence of an infant 12 within the field of view of the camera. The camera 42 can comprise a digital camera adapted to generate still shots and/or full motion video. The controller 32 may implement the still shots or the full motion video to determine the presence of the infant 12. The camera 42 could detect either visual light or infrared radiation depending on design considerations.

The system 40 further includes a motion sensor 46 that communicates with the controller 32 over the communication line 48. The motion sensor 46 may comprise any known technology adapted to monitor the motion of the infant 12 and to transmit the recorded motion data to the controller 32. In a non-limiting manner, the motion sensor 46 may comprise a mechanical device, an electrical device, an optical device, an acoustic device or a magnetic device configured to monitor motion in a known manner.

The system further includes a microphone 50 adapted to record sound from the infant 12 and transmit the recorded sound data to the controller 32 over the Communication line 52. The microphone 50 can be any one of multiple models and designs and can be positioned in various locations within the infant care device.

The system 40 can further include a pulse oximeter 54 that includes a sensor positioned on the infant 12. The sensor of the pulse oximeter 54 monitors the oxygen level in the patient's blood in a known manner and communicates this information to the controller 32 over the communication line 56.

In the embodiment shown in FIG. 2, the system 40 can further include a temperature sensor 58 that is positioned on the patient to provide a signal to the controller 32 along communication line 59. The temperature sensor 58 can be any one of as multitude of currently available temperature sensors.

Although various different sensors are shown in the embodiment of FIG. 2, it should be understood that additional sensors and other types of sensors could be utilized while operating within the scope of the present disclosure. Additionally, the infant presence sensing system 40 can be configured including less than all of the sensors and monitors shown in FIG. 2. The controller 32 receives the signals from each of the individual sensors and can make a determination, based upon the signals, whether an infant 12 is present on the infant platform 24. Based upon this determination by the controller, the controller 32 can control the operation of the infant care device 10.

Figure 3:
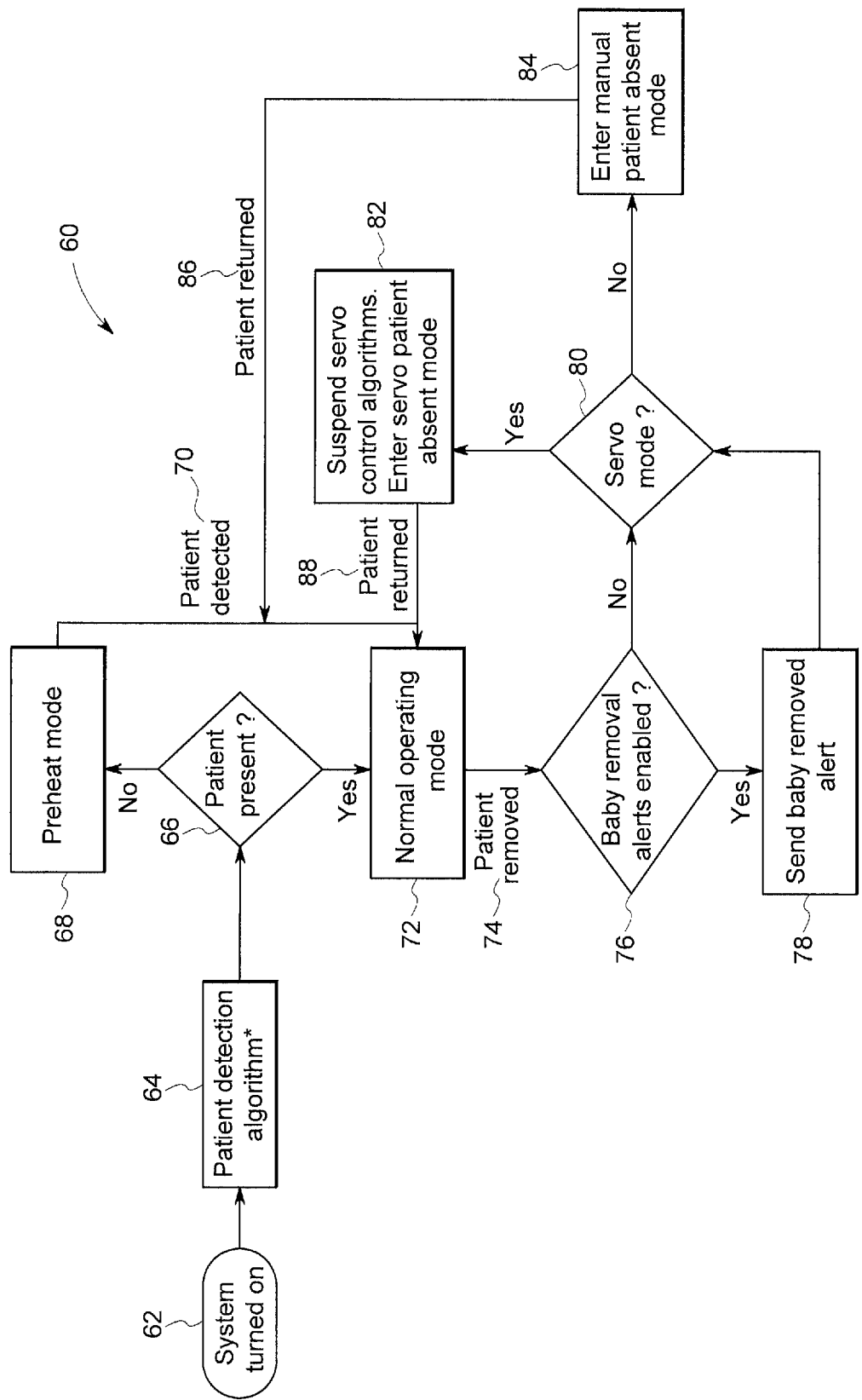
FIG. 3 is a flowchart illustrating a method of operating, the infant care device in accordance with the present disclosure.

Having described exemplary components of the infant presence sensing system 40 of the infant care device 10, a method of implementing the system to control the operation of the infant care device will now be described with reference to the flowchart of FIG. 3. The flowchart of FIG. 3 illustrates an operating algorithm 60 in accordance with one embodiment of the disclosure. It should be understood that other operating algorithms could be utilized while operating within the scope of the present disclosure. The technical effect of the algorithm 60 is to automatically determine whether an infant is present within the infant care device and, based upon this determination, automatically control the operation of the infant care device. The individual blocks shown in the algorithm 60 are performed by the controller 32 of FIG. 2 and the steps do not necessarily need to be performed in the order shown.

Referring now to FIG. 3, in step 62, the infant care device 10 is initially activated. In currently available infant care devices, the controller of the infant care device assumes that when the system is initially turned on, an infant is not present within the infant care device in accordance with the algorithm 60 shown in FIG. 3, the controller initiates a patient detection algorithm in step 64 following the initial activation of the infant care device. The patient detection algorithm shown in step 64 is carried out by the controller to determine the infant presence state of the infant care device. Specifically, the controller 32 utilizes the patient detection algorithm to determine whether the infant care device is occupied or unoccupied by an infant.

The patient detection algorithm can utilize the signals received from the multiple sensors shown in FIG. 2 to determine if an infant is present in or on the infant care device. The algorithm may use any combination of the signals from the sensors, such as a reading from the scale 34, a visual indication from the camera 42, signals from the motion detector 46, or signals from the physiological sensors (temperature sensor 58 and pulse oximeter 54) to determine whether the patient is present within the infant care device. It is contemplated that the signal from the camera 42 could be used alone and may be the most effective signal in determining the presence of the infant. Although not shown in FIG. 2, the controller 32 can also receive a manual input from a caregiver indicating whether the infant care device is either occupied or unoccupied.

Based upon the results of the patient detection algorithm in step 64, the controller determines in step 66 whether an infant is present within the infant care device. If the system determines that an infant is not present at the initial startup, the controller proceeds to step 68 and operates the infant care device in a preheat mode. In the preheat mode, the controller operates the radiant heater at a set value for a set amount of time to warm the infant care device. As an illustrative example, the radiant heater may be operated at 100% for a period of seven minutes. After this initial phase, the radiant heater is operated at a reduced set value (such as 25-50%) indefinitely until an infant is admitted to the infant care device. Preheating provides a warm environment such that when an infant is ready to be placed into the infant care device, the micro environment does not need to be heated quickly. In the preheat mode, various infant alarm parameters are suppressed since an infant is not present in the infant care device. The suppression of the alarms in the preheat mode reduces the number of nuisance alarms generated by the infant care device, thus reducing alarm fatigue.

As illustrated in FIG. 3, the controller causes the infant care device to remain in the preheat mode until the infant presence state changes, thereby indicating the presence of an infant in the infant care device, as illustrated by step 70. The determination that an infant is present can be made by the controller based upon either a single signal from the sensors or a combination of the signals from the various sensors shown in FIG. 2. Once the controller determines that an infant has been detected, the controller moves to step 72 in which the infant care device is operated in a normal operating mode. In the normal operating mode, the controller utilizes that alarm parameters set by the user and operates the heating elements to maintain the temperature in the infant care devices at a selected temperature. Various different normal operating modes are possible and are currently known to those of ordinary skill in the art. The first time the controlled enters the normal operation mode, the controller will also start an APGAR timer. Each time infant presence state changes to indicate an infant is now present on the infant platform, the controller will activate infant charting and trending events.

If the controller determines in step 66 that a patient is present upon startup, the system immediately proceeds to step 72 and begins to operate in the normal operating mode. Unlike prior control systems that assume a patient is not present at startup, the algorithm 60 makes a determination in step 66 whether an infant is present and, based upon this determination, whether the infant care device should be operated in the preheat mode or the normal operating mode. If an infant is present, the controller moves to the normal operating mode in which the temperature within the infant care device is controlled to a user selected value and alarm parameters are activated in accordance with settings from the caregiver.

When the infant care device is operating in the normal operating mode of step 72, the controller continues to monitor signals received from the various sensors shown in FIG. 2. If the controller 32 determines that the infant presence state changes, as indicated by step 74, the controller moves to step 76 and determines whether the baby removal alerts have been enabled or disabled. The baby removal alerts can include various different alerts that are generated upon the removal of the infant from the infant care device. The baby removal alerts of step 76 allow the algorithm 60 to selectively send alerts to a nursing station, a floor monitor, an individual caregiver or another location in the hospital, as indicated in step 78. The baby removal alerts act to enhance the security for the hospital, which is becoming an ever increasing concern. The baby removed alert shown in step 78 could also cause an alarm to activate at the infant care device along with sending alerts to a nursing station or other location within the hospital.

If the algorithm 60 determines in step 76 that the baby removal alerts have been disabled, the system does not generate an alert and instead proceeds to step 80 in which the controller determines whether the system is operating in the servo mode. The servo mode refers to a method of operating the infant care device to maintain the temperature of the infant at a desired level. As an example, the caregiver may set the desired temperature of the baby at 36.5° C. The controller will operate the heating units of the infant care device to maintain the temperature of the infant at this setting. Since the servo mode shown in step 80 is driven based upon the temperature of the infant, when the algorithm 60 determines that the infant has been removed and the infant care device is being operated in servo mode, the system proceeds to step 82. In step 82, the controller suspends the servo control algorithm and enters into a separate servo patient absence mode. In this state, the controller will control the heating units within the infant care device to maintain the temperature within the infant care device at the temperature when the infant was removed. The temperature within the infant care device is maintained at this constant value such that when a patient is returned, the temperature within the infant care device is close to the desired temperature needed to maintain the infant at the set temperature value. In addition to the temperature, the controller also suppresses some of the alarm conditions which are only relevant when the patient is present. The suppression of the alarms again reduces in the number of nuisance alarms and alarm fatigue that can occur in a crowded hospital environment If the system determines in step 80 that the infant care device is not being operated in the servo mode, the system proceeds to step 84. In an embodiment in which the infant care device is not being operated in a servo mode, the controller is controlling the heating units to maintain the temperature within the infant care device at a preselected value. When the patient is no longer present, the system proceeds to step 84 in which the temperature within the infant care device is lowered and maintained. In addition to the temperature, the controller also suppresses some of the alarm conditions which are only relevant when the patient is present. The suppression of the alarms again reduces in the number of nuisance alarms and alarm fatigue that can occur in a crowded hospital environment.

The algorithm 60 remains in either the servo patient absence mode shown in step 82 or the manual patient absence mode shown in step 84 until the controller determines that the infant has been returned, as shown by steps 86 and 88. If the controller determines that the infant has been returned, the controller returns to the normal operating mode shown in step 72. As can be understood by the flowchart of FIG. 3, the controller continues to monitor whether the infant is present within the infant care device and, based upon a detection of the return of the infant, returns operation to the normal operating mode. Once the algorithm returns to the normal operating mode of step 72, the controller continues to monitor the signal from the sensor to determine if the patient is again removed, as illustrated by step 74. This process continues and allows the infant care device to operate based upon whether or not the infant is present within the infant care device.

As can be understood by the above flowchart, the system and method of the present disclosure continuously monitors for the presence of an infant in the infant care device and, based upon a change in the infant presence state, adjusts the operation of the infant care device. Thus, every time the infant is placed on the infant platform or removed from the infant platform, the controller of the infant care device will adjust the operation of the infant care device. In addition to sensing the presence or absence of the infant, the system can also include a manual input that allows a care giver to provide information to the controller as to the presence or absence of the infant within the infant care device.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. An infant care device comprising:
an infant platform to support an infant;
a sensor configured to sense an infant presence state of the infant platform; and
a controller in communication with the sensor, wherein the controller is configured to:
begin or stop at least one of infant charting and trending related to monitored physiological parameters based on a change in the infant presence state; and
adjust alarm parameters based on the change in the infant presence state.

2. The infant care device of claim 1, wherein the sensor is a pressure sensor.

3. The infant care device of claim 2, wherein pressure sensor includes a load cell.

4. The infant care device of claim 1, wherein the sensor is a camera.

5. The infant care device of claim 4, wherein the camera is selected from an infrared camera and a video camera.

6. The infant care device of claim 1, wherein the sensor is a motion detector.

7. The infant care device of claim 1, wherein the controller is further configured to begin an APGAR timer the first time the infant presence state is occupied.

8. A method of operating an infant care device, comprising:
receiving a signal from at least one sensor at a controller, wherein the signal indicates a presence state of the infant care device, wherein the presence state is either occupied or unoccupied;
operating the infant care device based upon the presence state;
continuing to monitor the signal from the at least one sensor to continually determine the presence state;
sensing a change in the presence state from occupied to unoccupied;
operating the controller to adjust alarm parameters and heating algorithms; and
stop at least one of infant charting and trending related to monitored physiological parameters of the infant care device based on the change in the presence state from occupied to unoccupied.

9. The method of claim 8, further comprising the steps of:
determining the presence state of the infant care device upon initial startup; and
operating the infant care device in either a preheat mode or a normal mode based upon the presence state upon startup.

10. The method of claim 8, further comprising the step of generating an alert based upon a change in the presence state from occupied to unoccupied.

11. The method of claim 8, wherein the sensor is one of a camera, motion detector, temperature sensor or pressure sensor.

12. An infant care device comprising:
an infant platform to support an infant;
at least one sensor configured to generate a signal indicating whether the infant platform is either occupied or unoccupied; and
a controller in communication with the at least one sensor, wherein the controller is programmed to:
receive the signal from the at least one sensor;
control the operation of the infant care device based upon whether the infant platform is occupied or unoccupied;
continuously monitor the signal from the at least one sensor;
sense a change in the presence state from occupied to unoccupied; and
modify the operation of the infant care device by adjusting a heating algorithm from a servo mode to a steady temperature at which the infant care device was last at prior to the sensed change in the presence state from occupied to unoccupied.

13. The infant care device of claim 12, further comprising a plurality of sensors selected from the group consisting of a camera, a motion detector, a temperature sensor and a pressure sensor.

14. The infant care device of claim 12, wherein the controller is further configured to generate an alarm based upon a change from occupied to unoccupied.

* * * * *